United States Patent [19]

Singhal et al.

[11] Patent Number: 5,985,680
[45] Date of Patent: Nov. 16, 1999

[54] METHOD AND APPARATUS FOR TRANSFORMING A SUBSTRATE COORDINATE SYSTEM INTO A WAFER ANALYSIS TOOL COORDINATE SYSTEM

[75] Inventors: Ajay Singhal, Santa Clara; Yuri Uritsky, Newark, both of Calif.; Patrick D. Kinney, Coon Rapids, Minn.

[73] Assignee: Applied Materials, Inc., Santa Clara, Calif.

[21] Appl. No.: 08/907,590

[22] Filed: Aug. 8, 1997

[51] Int. Cl.$^6$ ..................................................... H01L 21/00
[52] U.S. Cl. .................................. 438/7; 438/12; 438/14; 438/16; 364/468.28; 356/375
[58] Field of Search .................................... 438/7, 10, 12, 438/14, 16, 17; 364/468.17, 468.28; 356/375

[56] References Cited

U.S. PATENT DOCUMENTS

| | | | |
|---|---|---|---|
| 4,819,167 | 4/1989 | Cheng et al. | 364/167.05 |
| 5,267,017 | 11/1993 | Uritsky et al. | 356/375 |
| 5,381,004 | 1/1995 | Uritsky et al. | 356/375 |
| 5,422,724 | 6/1995 | Kinney et al. | 356/375 |
| 5,474,640 | 12/1995 | Ye et al. | 156/345 |
| 5,497,007 | 3/1996 | Uritsky et al. | 250/491.1 |
| 5,598,341 | 1/1997 | Ling et al. | 364/468.17 |
| 5,628,870 | 5/1997 | Ye et al. | 438/729 |
| 5,761,064 | 6/1998 | La et al. | 364/468.17 |
| 5,841,661 | 12/1998 | Buchanan et al. | 364/468.28 |
| 5,870,187 | 2/1999 | Uritsky et al. | 356/398 |
| 5,909,276 | 6/1999 | Kinney et al. | 356/336 |

*Primary Examiner*—Kevin M. Picardat
*Attorney, Agent, or Firm*—Thomason, Moser & Patterson

[57] ABSTRACT

A method and apparatus for accurately transforming coordinates within a first coordinate system (e.g., a two-dimensional coordinate system associated with a substrate (or portion thereof)) into coordinates in a second coordinate system (e.g., a three-dimensional coordinate system of substrate (or portion thereof) tilted within a wafer analysis tool.

18 Claims, 3 Drawing Sheets

METHOD AND APPARATUS FOR TRANSFORMING A SUBSTRATE COORDINATE SYSTEM INTO A WAFER ANALYSIS TOOL COORDINATE SYSTEM

BACKGROUND OF THE DISCLOSURE

1. Field of the Invention

The invention relates to semiconductor wafer processing equipment and, more particularly, to a method and apparatus for tracking the location of defects on a substrate, e.g., a semiconductor wafer or a cleaved portion of a semiconductor wafer, by transforming a substrate coordinate system into a wafer analysis tool coordinate system.

2. Description of the Background Art

Identifying defects on the surface of a semiconductor wafer, such as particulate contaminants and other surface irregularities such as grain structure, is extremely important to integrated circuit manufacturing processes. To eliminate defect sources, defects are identified and analyzed to determine the source of the defect. Thereafter, corrective action can be taken to reduce or eliminate the defect source.

Typically, a defect identification process is accomplished in two steps. First, a laser scanner device scans a wafer with a laser and analyzes the backscatter from the wafer to locate defects on the surface of the wafer. One such laser scanner device is a Tencor SurfScan 6200, manufactured by Tencor Instruments. Secondly, the defect is analyzed to identify the root cause of the defect. The most commonly applied analysis tool is a high magnification imaging system such as a scanning electron microscope (SEM) which is used to identify the defect and/or the source of the defect by inspecting the defect at high magnification. Additionally, the SEM may be accompanied by instrumentation for performing chemical analysis of the defect. Such instrumentation includes an energy dispersive x-ray (EDX) detector. Other tools may include an Auger analysis device, atomic force microscope (AFM), optical spectroscopy device, electron backscattering detector and the like.

Many of these analysis tools can not physically accommodate an entire wafer within the analysis chamber of the tool. As such, the wafer is cleaved into manageable portions and each portion is analyzed separately within the instrumentation. One problem with cleaving a wafer into smaller individual portions and then attempting to analyze each portion is that the defect identified by the laser scanner device is identified in a coordinate system for the wafer as a whole as identified by the laser scanner device. Consequently, when the portion containing the defect is cleaved and placed within the analysis instrumentation, the coordinate system of the wafer that identifies the location of the defect is meaningless and the defect is not readily identifiable and positionable within the field of view of the analysis instrumentation. As such, the wafer analysis instrumentation must scan the entire portion of the wafer to find the defect for analysis.

A solution to this problem is disclosed in commonly assigned U.S. patent application Ser. No. 08/850,954 filed May 5, 1997 (Attorney Docket No. 1785) and incorporated herein by reference. This patent application discloses a method and apparatus for selectively marking defects on a semiconductor wafer. This apparatus fiducializes the wafer such that a two-dimensional wafer coordinate system is generated, then fiducializes the defects on the wafer identifying each defect and selectively marks each defect with an identifiable set of marks. These marks are readily visible via a two-dimensional, wafer analysis tool such that the defect can be easily located and analyzed. As such, when the wafer is cleaved into small portions, each portion containing a defect will have readily identifiable marks surrounding the defect.

Furthermore, the marks themselves can be used as a two-dimensional defect coordinate system for each defect that is contained within a cleaved portion of the wafer. As such, each wafer portion contains a two-dimensional coordinate system for the defect on that portion. The defect is known to be located a predefined distance from the marks. Consequently, a computer file can be generated for each portion of the wafer cleaved from an entire wafer that contains the two-dimensional coordinates of the defects on that portion relative to the defect marking coordinates (i.e., the defect coordinate system).

Although the method and apparatus for selectively marking a semiconductor wafer of U.S. patent application Ser. No. 08/850,954 filed May 5, 1997 (Docket 1785) provides an accurate, two-dimensional coordinate system for a defect and/or a cleaved portion of a semiconductor wafer, there are instances where the coordinate system requires transformation to conform to a particular analysis tool. For example, if the analysis tool is an electron backscattering diffraction (EBSD) analysis tool, the cleaved wafer is generally inserted into the analysis chamber at an angle relative to a horizontal plane. By analyzing the wafer portion tilted at an angle, the EBSD analysis tool has a small footprint within the laboratory and also promotes substantial electron backscattering due to the angle of incidence of the electron beam that scans the wafer portion. Other spectroscopic techniques such as Auger electron spectroscopy, optical spectroscopy and SEM may also tilt the wafer portion to achieve substantially improved signal strength and signal bandwidth. By tilting the wafer portion, the two-dimensional coordinate system associated with that portion is now distorted. Consequently, the defect is no longer directly identifiable by the two-dimensional coordinates of the wafer portion.

Furthermore, the analysis tool depth of field is limited and as such, the tool can only focus upon a small portion of the wafer. Thus, to find defect locations, not only must the tool scan in two dimensions, the tool must scan in a third dimension (focus) to maintain the surface within the depth of field of the tool.

Therefore, there is a need in the art for a method and apparatus that transforms the two-dimensional coordinate system associated with a tilted a wafer (or portion thereof) into a three-dimensional coordinate system of a wafer analysis tool.

SUMMARY OF THE INVENTION

The invention overcomes the disadvantages associated with the prior art by providing a method and apparatus that accurately transforms the two-dimensional coordinate system associated with a substrate, e.g., full semiconductor wafer or a cleaved portion of a semiconductor wafer, into a new, three-dimensional coordinate system for the substrate as tilted within an analysis tool.

More specifically, the method and apparatus of the present invention fiducializes a wafer, providing a wafer coordinate system. Thereafter, defects are located upon the wafer using a wafer marking tool. Once the defects are found, each defect is fiducialized and marked with identifiable marks that are located proximate each defect. Thereafter, the wafer is optionally cleaved to provide small portions of the wafer for analysis within a defect analysis tool. Each portion of the wafer is then moved to an analysis tool for further analysis.

Once the angle at which the wafer portion will be positioned within the analysis tool is known, the two-dimensional coordinates of the portion that are based on the defect coordinates are transformed into a new, three-dimensional coordinate set for the inclined wafer portion. From this coordinate set, the position of the defect is readily found and analyzed by the defect analysis tool.

A wafer is cleaved in accordance with the invention using a wafer marking tool that contacts the wafer surface to indent (mark) the surface. To produce a scribe line along which the wafer is to be cleaved, the marking head of the wafer marking tool is accurately positioned above the wafer. The tip of the marking head is lowered to impact the wafer surface, then the wafer is linearly moved to form a small scribe line. To facilitate cleaving a large wafer, the scribing process can be repeated to form a plurality of linearly aligned scribe lines along which the wafer will be cleaved. The wafer is then removed from the marking tool and broken along the scribe line (s). By placing four scribe lines that are perpendicular to one another about a portion of a wafer to be cleaved, where each scribe line is accurately positioned at known coordinate locations using the marking tool, a coordinate system for the cleaved portion relative to the wafer coordinate system is accurately known. As such, two of the cleaved edges of the portion are used as the x and y axes of the coordinate system for the cleaved portion.

Although the invention, up to this point, has been discussed in the context of an inclined cleaved portion of a wafer, the inventive coordinate system transformation is also applicable to mapping two-dimensional coordinates on a full wafer to three-dimensional coordinates on a full wafer within a wafer analysis tool. As such, the transformation can be used when analysis instrumentation is able to accommodate a full-sized wafer.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
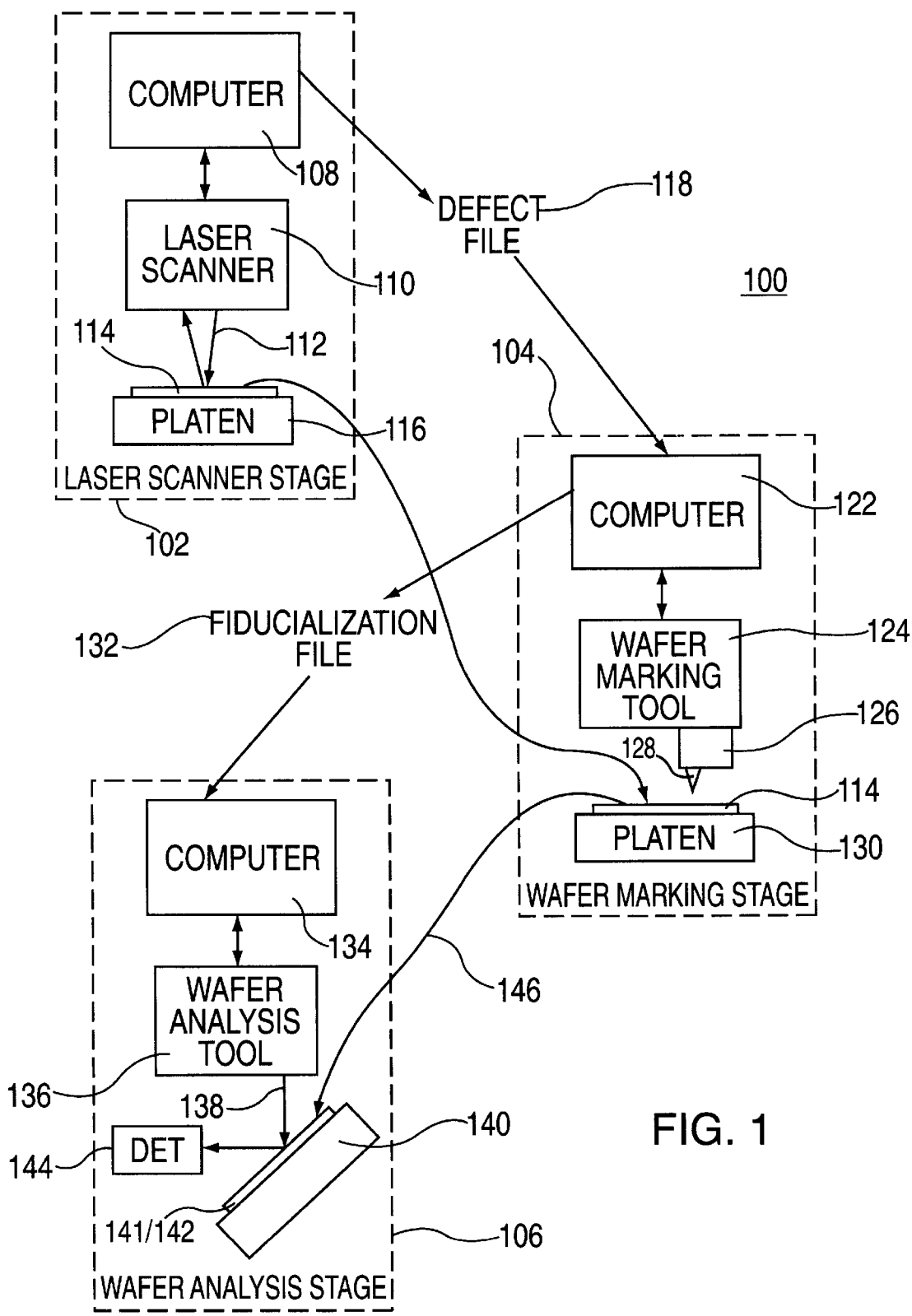
FIG. 1 depicts a schematic view of a wafer scanning, marking and analysis system that is operated in accordance with the present invention.

FIG. 1 depicts a schematic view of a suite of equipment that forms a system 100 that operates in accordance with the present invention to scan, mark and analyze a substrate (e.g., a semiconductor wafer or portion thereof). Specifically, the system 100 contains a laser scanner stage 102, a wafer marking stage 104 and a wafer analysis stage 106. The laser scanner stage 102 contains a laser scanner 110 for scanning a wafer 114 with a laser beam 112 and a computer 108 for controlling the laser scanning process as well as accumulating and storing the scan results. The laser scanner 110 further contains a platen 116 for retaining the wafer 114 in a stationery position during the laser scanning process. The laser scanner 110 and its associated computer 108 create a computer file 118 (a tabular defect file) that identifies a coordinate system for the wafer 114 as well as identifies the locations of defects on the wafer 114 relative to the wafer coordinate system and an estimated size of each defect. The laser scanner stage 102 illustratively comprises a Tencor SurfScan 6200 laser scanner coupled to a personal computer.

Once the laser scanner stage 102 has completed the scanning process and generated a defect file 118 for the wafer 114, the wafer 114 and its defect file 118 are moved to the wafer marking stage 104. The wafer is physically carried (arrow 120) from the laser scanner stage 102 to the wafer marking stage 104; however, the defect file may either be transferred using a removable storage medium such as a floppy disk or may be transferred electronically through a computer network.

The wafer marking stage 104 comprises a wafer marking tool 124 and an associated computer 122 for controlling the wafer marking process. Preferably, marking is accomplished by a physical indentation of the wafer 114 as defined in "The Method And Apparatus For Selectively Marking A Semiconductor Wafer", U.S. patent application Ser. No. 08/850,954 filed May 5, 1997 (Attorney Docket No. 1785) and incorporated herein by reference. The wafer marking stage described in this patent application is manufactured as the MICROMARK 5000 Avanced Defect Review System by MicroTherm, LLC of Minneapolis, Minn. In that illustrative system, the wafer marking tool 124 has a marking head 126 that supports a marking tip 128. The marking tip is manufactured from a relatively hard substance such as diamond such that an indentation can be made in a semiconductor wafer without generating excess particulate contaminants. The computer 122 controls the wafer marking tool 124 its marking tip 128 over selected locations on the wafer 114. The wafer is vacuum chucked to a platen 130. Once the tip 128 is positioned, the computer 122 causes the tip 128 to impact the wafer 114 and form an indentation. The computer also fiducializes the wafer 114 and computes an accurate wafer coordinate system within which all wafer features, including marks and defects, can be readily identified. The computer 122 produces a computer file 132 (a fiducialization file) containing the defect file information from the laser scanner stage 102 as well as the wafer mark locations and an accurate wafer coordinate system. The defect file information from the laser scanner stage may be updated to reflect the more accurate wafer coordinate system developed by the wafer marking stage. Furthermore, the wafer marking tool can also be used to create scribe lines on the wafer for cleaving the wafer into smaller portions. A more detailed description of the wafer marking process as well as the cleaving process is presented below with respect to FIG. 2. In lieu of using an indentation to mark the wafer surface, the selective marking of the wafer 114 may be accomplished using an ion gun or laser. In any event, the wafer 114 is marked with one or more readily identifiable surface marks on the wafer.

Once the wafer 114 is marked, the wafer 114, depending upon the sample size that can be accommodated by the wafer analysis stage 106, may be cleaved into smaller portions 142 or moved (arrow 146) as a whole 114 to the wafer analysis stage 106. In addition to moving the wafer (or portion thereof) to the stage 106, the fiducialization file 132 is transferred, either physically or electronically, to the wafer analysis stage 106.

The wafer analysis stage 106 contains a wafer analysis tool 136 and an associated computer 134. The wafer analysis tool 136 contains a platen 140 for retaining the wafer (or portion thereof) at an angle relative to the horizontal and a signal detector 144 for receiving the reflected analysis signal, e.g., a laser beam, an electron beam, optical emission, and the like. The computer 134 controls the wafer analysis tool 136 as well as accumulates and stores data collected by the detector 144. The fiducialization file 132 is used to position and focus, for example, an electron beam 138 upon the wafer (or portion thereof) 114/142. The invention, generally executed upon computer 134, maps the two-dimensional coordinates of the fiducialization file 132 onto a three-dimensional coordinate system of the tilted wafer within the wafer analysis tool coordinate system. This mapping function permits the wafer analysis tool 136 to be rapidly positioned and focused upon particular locations on the wafer without undo three-dimensional scanning of the beam 138.

Figure 2:
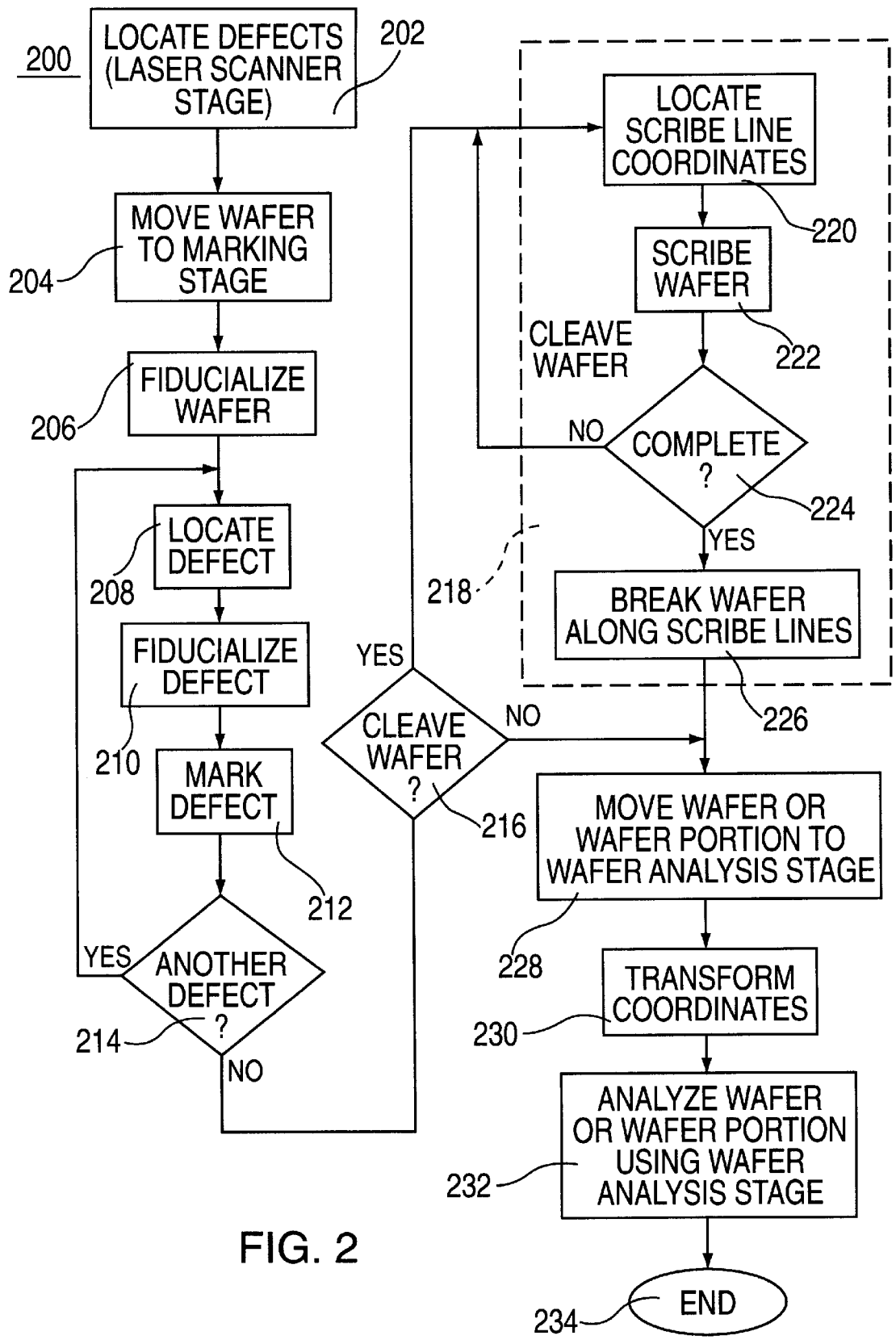
FIG. 2 depicts a flow diagram of the method of the present invention.

FIG. 2 depicts a flow diagram of the method 200 of the present invention as performed by the system of FIG. 1. The method 200 begins, at step 202, by scanning the semiconductor wafer with the laser scanner stage (102 in FIG. 1). The scanner creates a computer file (tabular defect file) that identifies a coordinate system for the wafer as well as identifies the locations of defects on the wafer relative to the wafer coordinate system and an estimated size of each defect. The wafer as well as the defect file are then moved, at step 204, to a wafer marking stage (104 in FIG. 1) wherein the wafer, in step 206, is fiducialized to the wafer coordinate system of the wafer marking stage. This fiducialization is required because the coordinate system of the laser scanning device may be different from and/or less accurate than the coordinate system of the wafer marking apparatus. As such, the wafer must be fiducialized to define a coordinate system for the wafer within the marking stage.

At step 208, a defect, identified within the laser scanner defect file, is located and processed by the wafer marking apparatus. The defect is fiducialized in step 110. Defect fiducialization provides for accurately adjusting (mapping) the wafer coordinate system and defect location coordinates to identify the defects relative to the wafer marking stage coordinate system.

At step 212, the identified defect is marked. Preferably, marking is accomplished by a physical indentation as defined in "The Method And Apparatus For Selectively Marking A Semiconductor Wafer", U.S. patent application Ser. No. 850,954 filed May 5, 1997 (Attorney Docket No. 1785) and herein incorporated by reference. Alternatively, the selective marking of the defect may be accomplished using an ion gun or laser. In any event, the defect is accurately marked with one or more readily identifiable surface marks on the wafer.

Figure 3:
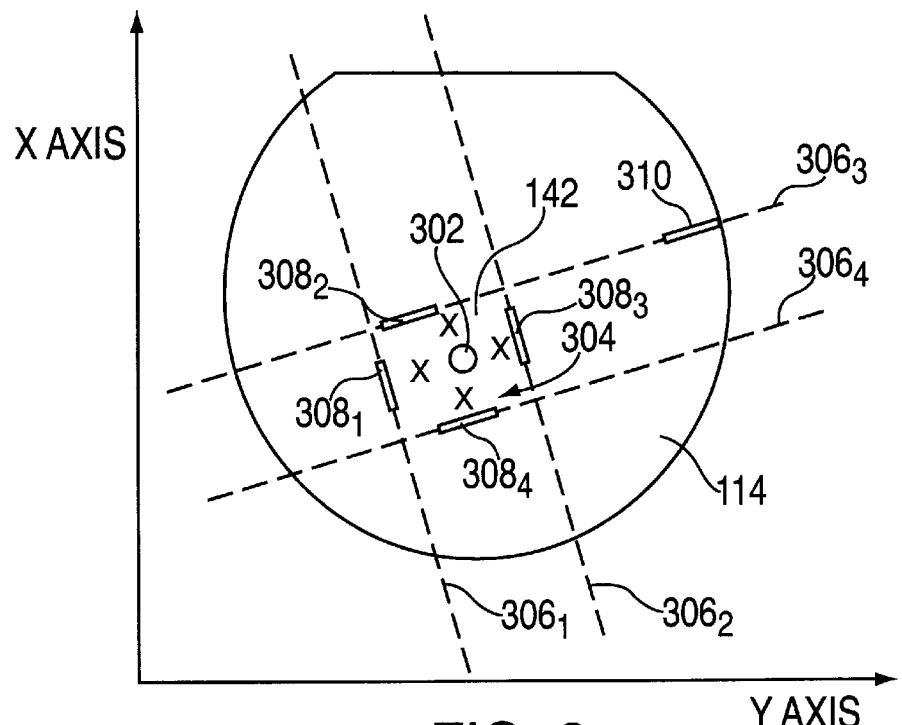
FIG. 3 depicts a top plan view of a semiconductor wafer marked in accordance with the present invention.

FIG. 3 depicts a semiconductor wafer 114 prior to being cleaved into one or more portions, where the defect 302 is positioned within a set of fiducialization marks 304 (shown as four X marks). In the illustrative example, there are four marks 304 that surround the defect 302 at locations that are approximately equidistant from the defect 302. As each mark is made, the fiducialization file is updated such that the file contains the defect file information from the laser scanner stage as well as the defect mark locations within the accurate marking tool coordinate system. Additionally, the defect file information may be updated to correct the coordinates to align them with the marking tool coordinate system.

Returning to FIG. 1, the method 200 queries, at step 214, whether another defect is to be fiducialized and marked. If the query is affirmatively answered, the method returns to step 208 to process another defect (i.e., locate and mark). However, if the query at step 214 is negatively answered, the method proceeds to step 216.

At step 116, the method 200 queries whether the wafer is to be cleaved. If the wafer analysis stage (106 of FIG. 1) can accommodate an entire wafer, then the query of step 216 is negatively answered and the method proceeds along the NO path to sub-process 228. However, if the wafer need to be cleaved the method proceeds from step 216 along the YES path to step 218 where the wafer is cleaved into portions that are sized to physically fit into a wafer analysis tool.

The wafer cleaving sub-process 218 begins at step 220 where the desired coordinates for a scribe line are positioned beneath a marking head of the marking tool. The marking head has a hard, sharp marking tip (e.g., a diamond tip) capable of scratching the wafer surface. Once scratched, the crystal structure of the wafer allows the wafer to break along a substantially straight line in the direction of the scratch. One or more scratches (scribe lines) along a straight line are sufficient to achieve an very accurate break. Since the marking tool places the scribe lines within a very accurate marking tool coordinate system, the edge of the cleaved portion will have accurate coordinates to form a cleaved portion coordinate system relative to the marking tool coordinate system.

More specifically, once a scribe location is located at step 220, the marking tool scratches the wafer at step 222. The scratch is formed by contacting the marking tip with the wafer surface and then linearly moving the tip in the direction of the desired break line. Either the tip can be moved as the wafer is maintained in a stationery position or vice versa.

At step 224, the cleaving process 218 queries whether all the scribe lines are complete. If the query is negatively answered, the method 200 proceeds to step 220 and creates another scribe line. Generally, as depicted in FIG. 3, four scribe lines $308_1$, $308_2$, $308_3$ and $308_4$ are used, each line defining a side of the cleaved portion 142 to produce a square or rectangular cleaved portion 142. To produce the straightest edge, it is recommended that at least two scribe lines be used to define each edge, with one of the scribe lines being near the wafer edge, e.g., scribe lines $308_2$ and 310. Cleaving lines, i.e., lines along which the wafer is broken, are shown as dashed lines $306_1$, $306_2$, $306_3$ and $306_4$.

Returning to FIG. 2, once all the scribe lines are formed, the method proceeds to step 226. At step 226, the wafer is physically broken along the scribe lines to form a cleaved portion containing the defect of interest.

Figure 4:
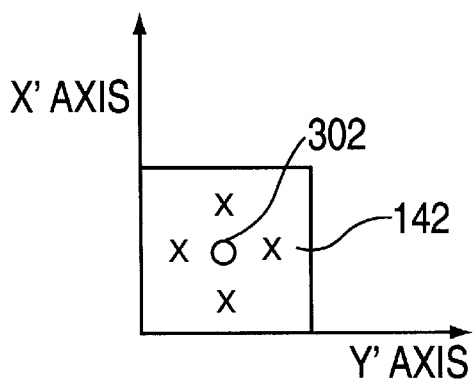
FIG. 4 depicts a cleaved portion of the semiconductor wafer of FIG. 3 containing a defect.

FIG. 4 depicts a cleaved portion 142 of the wafer 114 of FIG. 3, wherein the fiducialization marks 304 for the defect are proximate the defect 302. The portion coordinate system (x', y') can be established along lines intersecting the defect marks 304. As such, the defect coordinate system can be defined by the y' axis and the x' axis that pass through the mark locations irrespective of the location of the cleaving lines. However, the accurate cleaving lines provide an excellent, readily identifiable coordinate system for x and y axes of the portion coordinate system (x', y'). As such, FIG. 4 depicts the coordinate system defined by the X' axis and Y' axis aligned with two orthogonal edges of the portion 142.

Returning to FIG. 2, at step 228, the whole wafer 114 or the cleaved portion 142 of the wafer is moved to the wafer analysis stage (106 in FIG. 1). In addition to physically moving the wafer(or portion thereof) to the analysis stage, the fiducialization file that contains the coordinates of the defects, the coordinates of the defect marks and the scribe line coordinates is also moved to the computer associated with the wafer analysis tool. As such, the fiducialization file is used to align the analysis tool signal detector with the coordinates of the defect (or any other location on the wafer surface). The defect at this point is related to the two-dimensional fiducialization marks for the defect, i.e., the coordinate system defined by the X' and Y' axes of the edge coordinates.

Figure 5:
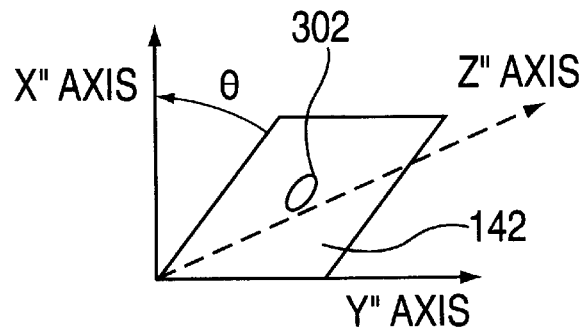
FIG. 5 depicts the cleaved portion of FIG. 4 within an tilted coordinate system of a defect analysis tool.

When the wafer is placed within the analysis tool, which tilts the portion of the wafer at an angle θ as shown in FIG. 5, the portion is inclined at an angle relative to the x'-y' plane such that the coordinate system of the wafer portion and the defect is now represented by x", y" and z", a three-dimensional coordinate system.

At step 230 of FIG. 2, the two-dimensional coordinate system of x', y' is transformed into the three-dimensional coordinate system x", y", z". This is accomplished using the following general equation:

$$\begin{bmatrix} x^t \\ y^t \\ z^t \end{bmatrix} = \begin{bmatrix} \alpha_x & \beta_x & \gamma_x \\ \alpha_y & \beta_y & \gamma_y \\ \alpha_z & \beta_z & \gamma_z \end{bmatrix} \begin{bmatrix} x^0 \\ y^0 \\ z^0 \end{bmatrix}$$

where:

$$\alpha_x = \cos(x^0 x^t) \quad \alpha_y = \cos(x^0 y^t) \quad \alpha_z = \cos(x^0 z^t)$$
$$\beta_x = \cos(y^0 x^t) \quad \beta_y = \cos(y^0 y^t) \quad \beta_z = \cos(y^0 z^t)$$
$$\gamma_x = \cos(z^0 x^t) \quad \gamma_y = \cos(z^0 y^t) \quad \gamma_z = \cos(z^0 z^t)$$

The coordinates $x^t, y^t, z^t$ are generalized three-dimensional coordinates defined within the coordinate system of the analysis tool, while the coordinates $x^0, y^0, z^0$ are generalized three-dimensional coordinates defined within the coordinate system of the wafer portion. The 3×3 matrix of the foregoing equation maps the wafer portion coordinates to the coordinates of the analysis tool. The operand of the cosine term represents the angle between the respective axes described by the operand, e.g., operand $(x^0 y^t)$ represents the angle between the $x^0$ axis and the $x^t$ axis. For a transformation from a two-dimensional coordinate system into a three-dimensional coordinate system, the $z^0$ term is zero and the foregoing equation transforms any x',y' coordinate into an x",y",z" coordinate.

At step 232, the defect analysis tool can quickly align the analysis head, beam or other analysis tool signal detector with the defect based upon the transformed coordinate system derived in step 230 using the forgoing equation. As such, the defect is readily identifiable, focused upon and can be quickly analyzed. The method 200 ends at step 234.

Since the wafer cleaver (e.g., using the marking tool to scribe the wafer) can offer a less than one micron accuracy and can cleave small pieces, e.g., 30 mm², the method of the present invention as described above can be simplified. Since the cleaving apparatus is capable of cleaving very accurately, a single mark to identify the location of a defect may be used. For example, once a defect is determined in the two-dimensional coordinate system (x',y') of the wafer marking apparatus, the defect can be marked with a single point proximate the defect. Thereafter, the marking tool can scribe the wafer along two axes at right angles that intersect at the marked point. That marked point then becomes the origin (0,0) for the coordinate system of the cleaved portion. Consequently, the cleavage planes along each edge that extend from the origin mark become the coordinate axes for the coordinate system of the cleaved portion and no further defect marking is necessary. The defects can be identified relative to the portion edges. Thereafter, the method operates in the same manner as discussed above to transform the two-dimensional coordinates of the cleaved portion into a three-dimensional coordinate system for identifying the defect within the defect analysis tool.

Although various embodiments which incorporate the teachings of the present invention have been shown and described in detail herein, those skilled in the art can readily devise many other varied embodiments that still incorporate these teachings.

What is claimed is:

1. A method of transforming a first coordinate system associated with a substrate into a second coordinate system associated with a wafer analysis tool comprising the steps of:

determining an angle at which the substrate is mounted within the wafer analysis tool;

transforming coordinates within the first coordinate system into coordinates within the second coordinate system; and using the transformed coordinate system to align the analysis tool with a particular location upon the substrate.

2. The method of claim 1 wherein the substrate is a semiconductor wafer.

3. The method of claim 1 wherein the substrate is a cleaved portion of a semiconductor wafer.

4. The method of claim 3 further comprising the steps of:

positioning a semiconductor wafer in a wafer marking tool;

identifying a plurality of scribe line locations;

scratching the surface of the semiconductor wafer at each scribe line location using a marking tip of said wafer marking tool; and breaking the wafer along said scribe lines to form said cleaved portion of said semiconductor wafer.

5. The method of claim 4 wherein a pair of orthogonal scribe lines respectively define an x axis and y axis of the cleaved portion.

6. The method of claim 1 wherein the transforming step further comprises the step of:

performing a coordinate transformation in accordance with:

$$\begin{bmatrix} x^t \\ y^t \\ z^t \end{bmatrix} = \begin{bmatrix} \alpha_x & \beta_x & \gamma_x \\ \alpha_y & \beta_y & \gamma_y \\ \alpha_z & \beta_z & \gamma_z \end{bmatrix} \begin{bmatrix} x^0 \\ y^0 \\ z^0 \end{bmatrix}$$

where:

$$\alpha_x = \cos(x^0 x^t) \quad \alpha_y = \cos(x^0 y^t) \quad \alpha_z = \cos(x^0 z^t)$$
$$\beta_x = \cos(y^0 x^t) \quad \beta_y = \cos(y^0 y^t) \quad \beta_z = \cos(y^0 z^t)$$
$$\gamma_x = \cos(z^0 x^t) \quad \gamma_y = \cos(z^0 y^t) \quad \gamma_z = \cos(z^0 z^t)$$

where $x^0, y^0, z^0$ define coordinates of the substrate coordinate system and $x^t, y^t, z^t$ define the coordinates in the wafer analysis tool coordinate system.

7. The method of claim 1 wherein the first coordinate system is a two-dimensional coordinate system and the second coordinate system is a three-dimensional coordinate system.

8. A method comprising the steps of:
positioning a semiconductor wafer in a wafer marking tool;
fiducializing the semiconductor wafer to define a first coordinate system;
identifying a plurality of scribe line locations within the first coordinate system;
scratching the surface of the semiconductor wafer at each scribe line location using a marking tip of said wafer marking tool;
breaking the wafer along said scribe lines to form said cleaved portion of said semiconductor wafer;
moving the cleaved portion of the semiconductor wafer to a wafer analysis tool;
determining an angle at which the substrate is mounted within the wafer analysis tool;
transforming the first coordinate system into a second coordinate system; and
using the transformed coordinate system to align the analysis tool with a particular location upon the substrate.

9. The method of claim 8 wherein a pair of orthogonal scribe lines respectively define an x axis and y axis of the cleaved portion within the first coordinate system.

10. The method of claim 8 wherein the transforming step further comprises the step of:
performing a coordinate transformation in accordance with:

$$\begin{bmatrix} x^I \\ y^I \\ z^I \end{bmatrix} = \begin{bmatrix} \alpha_x & \beta_x & \gamma_x \\ \alpha_y & \beta_y & \gamma_y \\ \alpha_z & \beta_z & \gamma_z \end{bmatrix} \begin{bmatrix} x^0 \\ y^0 \\ z^0 \end{bmatrix}$$

where:

$$\alpha_x = \cos(x^0 x^I) \quad \alpha_y = \cos(x^0 y^I) \quad \alpha_z = \cos(x^0 z^I)$$
$$\beta_x = \cos(y^0 x^I) \quad \beta_y = \cos(y^0 y^I) \quad \beta_z = \cos(y^0 z^I)$$
$$\gamma_x = \cos(z^0 x^I) \quad \gamma_y = \cos(z^0 y^I) \quad \gamma_z = \cos(z^0 z^I)$$

where $x^0, y^0, z^0$ define coordinates of the first coordinate system and $x^I, y^I, z^I$ define the coordinates in the second coordinate system.

11. Apparatus for transforming a first coordinate system associated with a substrate into a second coordinate system associated with a wafer analysis tool comprising:
a computer that executes an instruction set that determines an angle at which the substrate is mounted within the wafer analysis tool, transforms the first coordinate system into a second coordinate system, and uses the transformed coordinate system to align the analysis tool with a particular location upon the substrate.

12. The apparatus of claim 11 wherein the substrate is a semiconductor wafer.

13. The apparatus of claim 11 wherein the substrate is a cleaved portion of a semiconductor wafer.

14. The apparatus of claim 13 further comprising:
a wafer marking tool having a marking tip, where said marking tool fiducializes the semiconductor wafer to define a first coordinate system, identifies a plurality of scribe line locations within the first coordinate system, scratches the surface of the semiconductor wafer at each scribe line location using said marking tip.

15. The method of claim 14 wherein a pair of orthogonal scribe lines respectively define an x axis and y axis of the cleaved portion.

16. The method of claim 11 wherein the computer performs a coordinate transformation in accordance with:

$$\begin{bmatrix} x^I \\ y^I \\ z^I \end{bmatrix} = \begin{bmatrix} \alpha_x & \beta_x & \gamma_x \\ \alpha_y & \beta_y & \gamma_y \\ \alpha_z & \beta_z & \gamma_z \end{bmatrix} \begin{bmatrix} x^0 \\ y^0 \\ z^0 \end{bmatrix}$$

where:

$$\alpha_x = \cos(x^0 x^I) \quad \alpha_y = \cos(x^0 y^I) \quad \alpha_z = \cos(x^0 z^I)$$
$$\beta_x = \cos(y^0 x^I) \quad \beta_y = \cos(y^0 y^I) \quad \beta_z = \cos(y^0 z^I)$$
$$\gamma_x = \cos(z^0 x^I) \quad \gamma_y = \cos(z^0 y^I) \quad \gamma_z = \cos(z^0 z^I)$$

where $x^0, y^0, z^0$ define coordinates of the first coordinate system and $x^I, y^I, z^I$ define the coordinates in the second coordinate system.

17. The method of claim 11 wherein the first coordinate system is a two-dimensional coordinate system and the second coordinate system is a three-dimensional coordinate system.

18. Apparatus for cleaving and analyzing a semiconductor wafer comprising:
a wafer marking tool containing a marking tip, where said marking tool fiducializes the semiconductor wafer to define a first coordinate system, identifies a plurality of scribe line locations within the first coordinate system, scratches the surface of the semiconductor wafer at each scribe line location using said marking tip;
means for breaking the semiconductor wafer along said scribe lines to form a cleaved portion of said semiconductor wafer;
means for moving said cleaved portion to a wafer analysis tool;
means for transferring the first coordinate system from said wafer marking tool to said wafer analysis tool;
said wafer analysis tool containing a computer that executes an instruction set that determines an angle at which the substrate is mounted within the wafer analysis tool, transforms the first coordinate system into a second coordinate system, and uses the transformed coordinate system to align the analysis tool with a particular location upon the substrate.

* * * * *